US009697331B2

(12) United States Patent
Jablonski et al.

(10) Patent No.: US 9,697,331 B2
(45) Date of Patent: Jul. 4, 2017

(54) ADAPTABLE INFORMATION EXTRACTION AND LABELING METHOD AND SYSTEM

(71) Applicant: Codonics, Inc., Middleburg Heights, OH (US)

(72) Inventors: Timothy J Jablonski, Lakewood, OH (US); Alan Gilbert, Hudson, OH (US); Gary Keefe, Brecksville, OH (US)

(73) Assignee: CODONICS, INC., Middleburg Heights, OH (US)

( * ) Notice: Subject to any disclaimer, the term of this patent is extended or adjusted under 35 U.S.C. 154(b) by 167 days.

(21) Appl. No.: 13/844,391

(22) Filed: Mar. 15, 2013

(65) Prior Publication Data

US 2014/0117081 A1    May 1, 2014

Related U.S. Application Data

(63) Continuation-in-part of application No. 13/666,368, filed on Nov. 1, 2012, now abandoned.

(60) Provisional application No. 61/554,449, filed on Nov. 1, 2011.

(51) Int. Cl.
*G06F 19/10* (2011.01)
*G06Q 50/22* (2012.01)
*G06F 19/00* (2011.01)

(52) U.S. Cl.
CPC ........ *G06F 19/3456* (2013.01); *G06F 19/326* (2013.01); *G06Q 50/22* (2013.01)

(58) Field of Classification Search
CPC ... G06Q 50/22; G06F 19/3456; G06F 19/326; G06F 19/3462
See application file for complete search history.

(56) References Cited

U.S. PATENT DOCUMENTS

| | | | | |
|---|---|---|---|---|
| 4,682,299 | A * | 7/1987 | McIntosh | A61J 7/04 340/309.4 |
| 5,557,091 | A * | 9/1996 | Krummel | 235/462.08 |
| 5,883,370 | A * | 3/1999 | Walker | G06Q 50/24 235/375 |
| 6,098,892 | A * | 8/2000 | Peoples, Jr. | 235/494 |
| 6,155,485 | A * | 12/2000 | Coughlin | G06F 19/326 235/383 |
| 6,172,596 | B1 * | 1/2001 | Cesar et al. | 340/10.41 |
| 6,985,870 | B2 * | 1/2006 | Martucci et al. | 705/3 |
| 7,546,949 | B1 * | 6/2009 | Blanford | 235/462.07 |
| 7,770,797 | B2 * | 8/2010 | Weiner et al. | 235/462.25 |
| 8,019,471 | B2 * | 9/2011 | Bogash | G06F 19/3462 700/232 |
| 8,606,596 | B1 * | 12/2013 | Bochenko | G06Q 10/00 705/2 |

(Continued)

*Primary Examiner* — Daniel Walsh
(74) *Attorney, Agent, or Firm* — Pearne & Gordon LLP

(57) ABSTRACT

Disclosed is a computerized method and system for identifying a medicinal substance from a plurality of different machine-readable codes that are each compliant with a different coding standard. A code reader reads a machine-readable code and transmits a signal indicative of the machine-readable code in response. A recognition identifies the coding standard with which the machine-readable code complies. Based on the identification by the recognition unit, computer-executable instructions specific to decoding information according the identified standard are selected and executed to decode the information encoded pursuant to the identified coding standard.

7 Claims, 9 Drawing Sheets

(56) References Cited

U.S. PATENT DOCUMENTS

| | | | |
|---|---|---|---|
| 8,636,202 B2* | 1/2014 | Keefe et al. | 235/375 |
| 8,893,970 B2* | 11/2014 | Keefe | G06Q 50/22 235/375 |
| 9,058,435 B2* | 6/2015 | Keefe | G06F 17/40 |
| 2001/0017817 A1* | 8/2001 | De La Huerga | A61J 1/035 368/10 |
| 2001/0045461 A1* | 11/2001 | Schuessler | 235/462.07 |
| 2002/0011519 A1* | 1/2002 | Shults, III | 235/462.01 |
| 2002/0065685 A1* | 5/2002 | Sasaki | A61M 15/0065 705/3 |
| 2003/0024986 A1* | 2/2003 | Mazz et al. | 235/454 |
| 2003/0036983 A1* | 2/2003 | Hougen et al. | 705/28 |
| 2003/0080191 A1* | 5/2003 | Lubow | G06K 1/121 235/462.01 |
| 2003/0135388 A1* | 7/2003 | Martucci et al. | 705/2 |
| 2003/0149599 A1* | 8/2003 | Goodall | G06Q 50/22 705/2 |
| 2003/0174326 A1* | 9/2003 | Rzasa | G01J 3/02 356/326 |
| 2004/0088187 A1* | 5/2004 | Chudy | G06Q 10/10 705/2 |
| 2004/0111277 A1* | 6/2004 | Pearson | B65B 9/02 705/2 |
| 2004/0215486 A1* | 10/2004 | Braverman | 705/2 |
| 2005/0061890 A1* | 3/2005 | Hinckley | 235/494 |
| 2005/0121520 A1* | 6/2005 | Yamaguchi et al. | 235/462.09 |
| 2005/0216310 A1* | 9/2005 | Clements | G06F 19/327 705/3 |
| 2006/0054682 A1* | 3/2006 | de la Huerga | G06F 19/3462 235/375 |
| 2006/0255132 A1* | 11/2006 | Ortiz et al. | 235/383 |
| 2007/0007348 A1* | 1/2007 | Shah | 235/462.01 |
| 2008/0201173 A1* | 8/2008 | Takehara | G06Q 50/24 705/3 |
| 2008/0217392 A1* | 9/2008 | Weiner et al. | 235/375 |
| 2008/0223941 A1* | 9/2008 | Mrowiec | 235/494 |
| 2008/0314978 A1* | 12/2008 | Fedorko | G06F 19/3456 235/385 |
| 2009/0050698 A1* | 2/2009 | Storey et al. | 235/383 |
| 2009/0127326 A1* | 5/2009 | Rudeen | 235/375 |
| 2010/0030667 A1* | 2/2010 | Chudy et al. | 705/28 |
| 2011/0082115 A1* | 4/2011 | O'Donnell, Jr. | A61K 31/675 514/110 |
| 2011/0145054 A1* | 6/2011 | Chetty et al. | 705/14.38 |
| 2012/0086958 A1* | 4/2012 | Srnka et al. | 358/1.6 |
| 2012/0089411 A1* | 4/2012 | Srnka | G06Q 50/22 705/2 |
| 2013/0018356 A1* | 1/2013 | Prince | G06Q 50/24 604/506 |
| 2013/0092727 A1* | 4/2013 | Edwards | B65C 11/0289 235/375 |
| 2013/0105568 A1* | 5/2013 | Jablonski et al. | 235/375 |
| 2013/0173277 A1* | 7/2013 | Eller | G06Q 50/22 705/2 |
| 2013/0186950 A1* | 7/2013 | Keefe et al. | 235/375 |
| 2013/0191149 A1* | 7/2013 | Kolberg et al. | 705/3 |
| 2013/0327822 A1* | 12/2013 | Keefe | G06F 17/40 235/375 |
| 2014/0060729 A1* | 3/2014 | Srnka et al. | 156/250 |
| 2014/0117081 A1* | 5/2014 | Jablonski | G06F 19/326 235/375 |
| 2014/0238214 A1* | 8/2014 | Finken | B31D 1/026 83/886 |
| 2014/0361076 A1* | 12/2014 | Iantorno | G06F 19/3462 235/381 |
| 2015/0161558 A1* | 6/2015 | Gitchell | G06F 19/327 235/375 |
| 2015/0238460 A1* | 8/2015 | Mahalingam | A61K 45/06 514/1.3 |

\* cited by examiner

ADAPTABLE INFORMATION EXTRACTION AND LABELING METHOD AND SYSTEM

CROSS REFERENCE TO RELATED APPLICATIONS

This application is a continuation-in-part of prior application Ser. No. 13/666,368, filed Nov. 1, 2012, which claims the benefit of U.S. Provisional Application No. 61/554,449, filed Nov. 1, 2011, each of which is incorporated in its entirety herein by reference.

BACKGROUND OF THE INVENTION

1. Field of the Invention

This application relates generally to a method and system for extracting information from a computer-readable code and, more specifically, to a method and system for automatically recognizing a standard with which a computer-readable code conforms and extracting information pertaining to a substance utilized in providing health care to a patient according to the standard recognized.

2. Description of Related Art

Drugs and other medicinal substances to be administered to patients receiving medical attention are commonly delivered in vials or other suitable containers. An anesthesiologist, surgeon, treating physician, nurse, or other authorized party can draw the medicinal substance from such containers ahead of a time when the medicinal substance is to be administered to the patient. Several containers of each medicinal substance may be stocked in a pharmacy maintained at healthcare facilities to ensure the availability of the medicinal substances when needed. However, the inventory of medicinal substances maintained by the pharmacy varies as the medicinal substances are administered. Further, many medicinal substances are habit forming and prone to abuse. Thus, detailed records are maintained by the pharmacy to monitor and replenish depleted inventories when necessary and to detect misappropriated medicinal substances.

Traditional record-keeping systems have required a pharmacist or other technician to manually enter medicinal substances received by the pharmacy into a database. Upon receipt of the medicinal substances, the technician has traditionally been required to read the documentation accompanying the medicinal substances to manually identify the medicinal substances received. Such documentation has also commonly included additional information such as the quantity of the containers, the concentration of the medicinal substances, and other pertinent information expressed in human-readable alphanumeric characters.

But such record-keeping systems are laborious and prone to human error. The alphanumeric characters may be small, making it difficult for the technician to properly read all of the pertinent information. Further, the information about the medicinal substances may be expressed in a variety of different units of measurement, causing confusion on the part of the technician. Thus, technicians may erroneously read or misplace a decimal point, or make a mistake concerning the unit of measurement when taking inventory of the medicinal substances. Further, poor handwriting by the technician entering the medicinal substances into the pharmacy's inventory can lead to errors at a later date when the medicinal substances are to be administered to patients.

More recently, attempts have been made to apply computer-readable codes on documentation accompanying the medicinal substances. The computer-readable code typically encodes the name of the medicinal substance. To identify the medicinal substance a scanner or other compatible computer peripheral is employed to read the computer-readable code and extract the name of the corresponding medicinal substance. A few jurisdictions have established a standard format for the computer-readable code used for this purpose, but the standards established vary from jurisdiction to jurisdiction. Thus, a system adapted to read the code according to one standard, will not operate properly to read the code adhering to another standard, limiting such systems for use in a particular jurisdiction. And when supplies of a particular medicinal substance are short in one jurisdiction, it is common to order that medicinal substance from another jurisdiction, possibly one adhering to a different standard. When this occurs, entering the medicinal substance into the pharmacy's inventor and otherwise documenting the medicinal substance requires the manual recognition and entry of the pertinent information described above as being susceptible to human error.

BRIEF SUMMARY OF THE INVENTION

Accordingly, there is a need in the art for an adaptable information extraction and labeling method and system that can recognize a plurality of different coding standards of machine-readable codes adopted in different geographic locations for labeling medicinal substances. The method and system allow for extraction of at least an identification of a medicinal substance labeled with different machine-readable codes that are compliant with different coding standards.

According to one aspect, the subject application involves a computerized system for identifying a medicinal substance from a plurality of different machine-readable codes that are each compliant with a different coding standard. The computerized system includes a code reader that is operable to read a first machine-readable code compliant with a first coding standard and, in response, transmit a first signal that is indicative of the first machine-readable code. The code reader also reads a second machine-readable code compliant with a second coding standard that is different from the first coding standard and, in response, transmits a second signal that is indicative of the second machine-readable code. A recognition component makes a determination that the first machine-readable code conforms to the first coding standard the first signal is received and makes a determination that the second machine-readable code conforms to the second coding standard when the second signal is received. A storage component stores computer-executable instructions corresponding to each of the first and second coding standards and a medicinal-substance database that includes an identification of the medicinal substance to be identified. A selection component selects, as selected instructions, the computer-executable instructions corresponding to the first coding standard in response to the determination by the recognition component that the first machine readable code is compliant with the first coding standard. Further, the selection component selects the computer-executable instructions corresponding to the second coding standard in response to the determination by the recognition component that the second machine readable code is compliant with the second coding standard. A processing component performs a method according to the selected instructions to retrieve the identification of the medicinal substance from the medicinal-substance database.

According to another aspect, the subject application involves a method of identifying a medicinal substance from a plurality of different machine-readable codes that are each compliant with a different coding standard used to encode information pertaining to the medicinal substance. The method includes using a code reader operatively connected to a computer system to receive information from a machine-readable code labeling the medicinal substance and generating a signal indicative of the machine-readable code. The computer system evaluates the signal indicative of the machine-readable code to identify a compatible coding standard with which the machine-readable code complies from among the different coding standards available. The computer system then selects computer-executable instructions specific to the coding standard from among a library of available computer-executable instructions specific to each of the different coding standards. The library is stored on a computer-readable memory in communication with the computer system. The computer system also executes the computer-executable instructions specific to the coding standard to extract information relating to the medicinal substance according to the compatible standard. The information relating to the mechanical substance that is extracted includes at least an identification of the medicinal substance.

According to another aspect, the subject application also involves a method of labeling a primary package containing a medicinal substance. The method includes using a code reader operatively connected to a computer system to receive information from a machine-readable code labeling a secondary package in which a plurality of the primary packages containing the medicinal substance is received. The computer system interprets the information from the machine-readable code to identify the medicinal substance. The information from the machine-readable code is transmitted to be presented to an operator for confirmation purposes, allowing the operator to confirm an accuracy of the information. Supplemental information input by the operator to supplement the information received from the machine-readable code provided to the secondary package is also received. Label content comprising a primary machine-readable code that is to appear on a primary label to be applied to each of the primary packages is generated. The machine-readable code encodes at least a portion of the information from the machine-readable code provided to the secondary package and the supplemental information.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE SEVERAL VIEWS OF THE DRAWING(S)

The invention may take physical form in certain parts and arrangement of parts, embodiments of which will be described in detail in this specification and illustrated in the accompanying drawings which form a part hereof and wherein.

Figure 6:
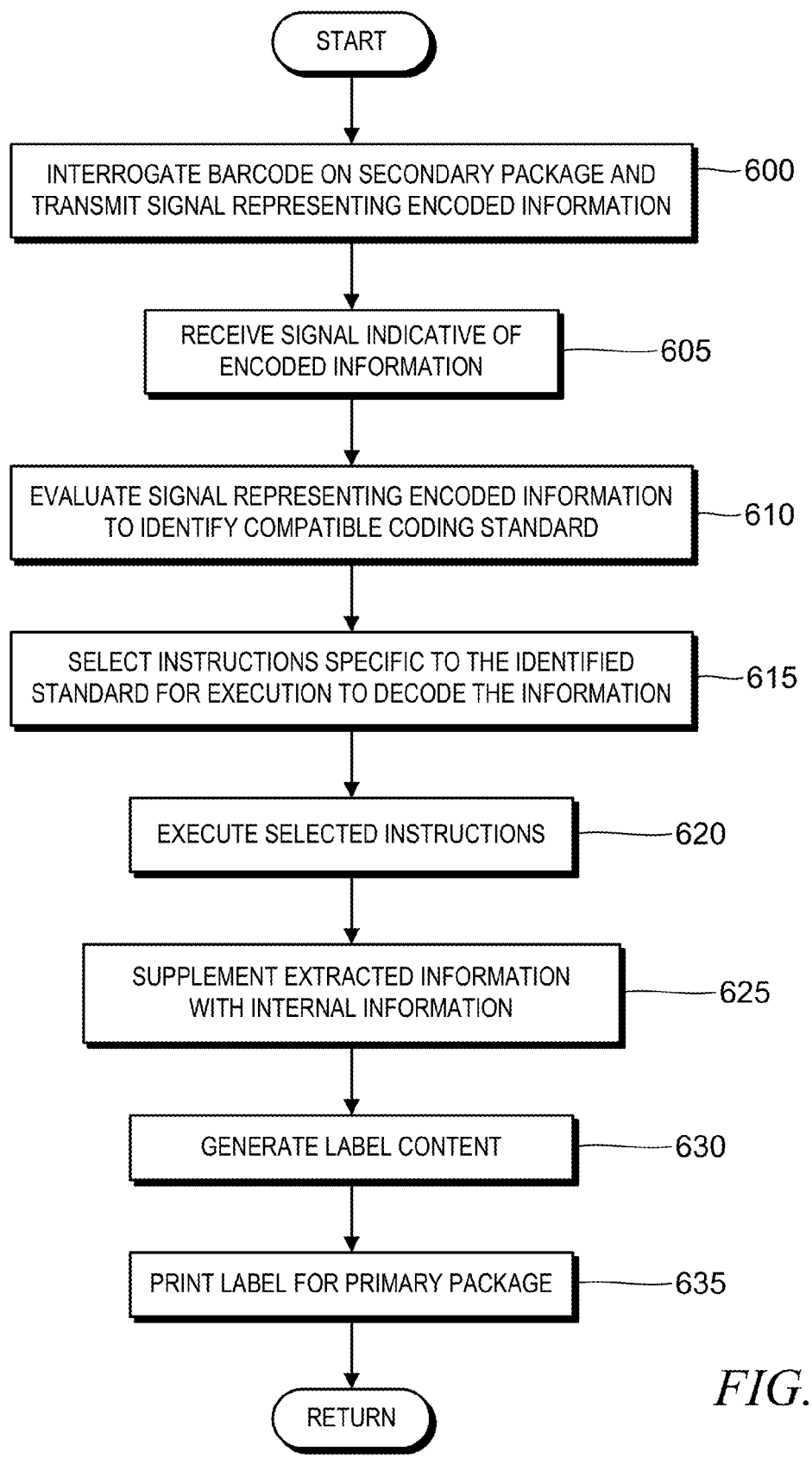
Figure 7:
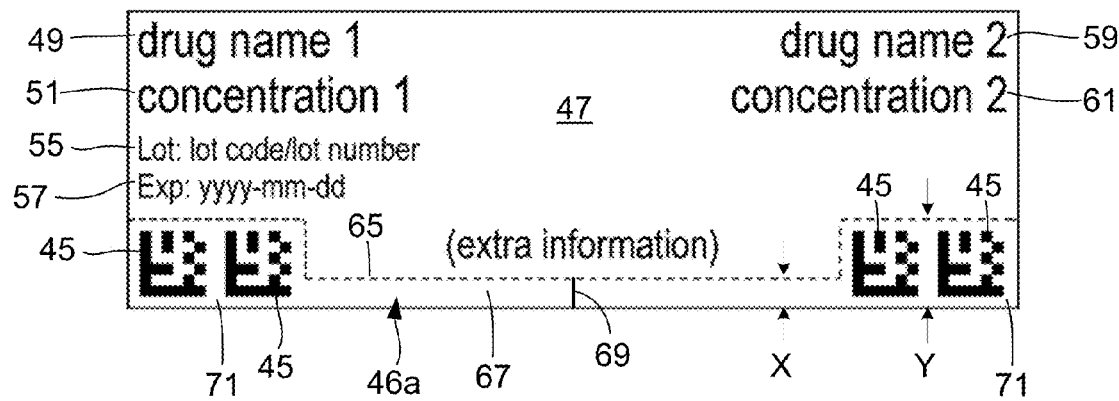
Figure 8:
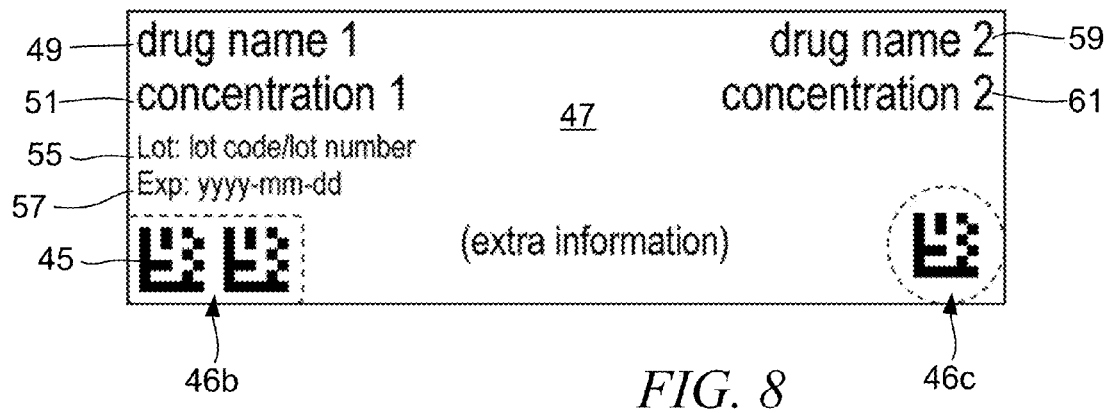
Figure 9:
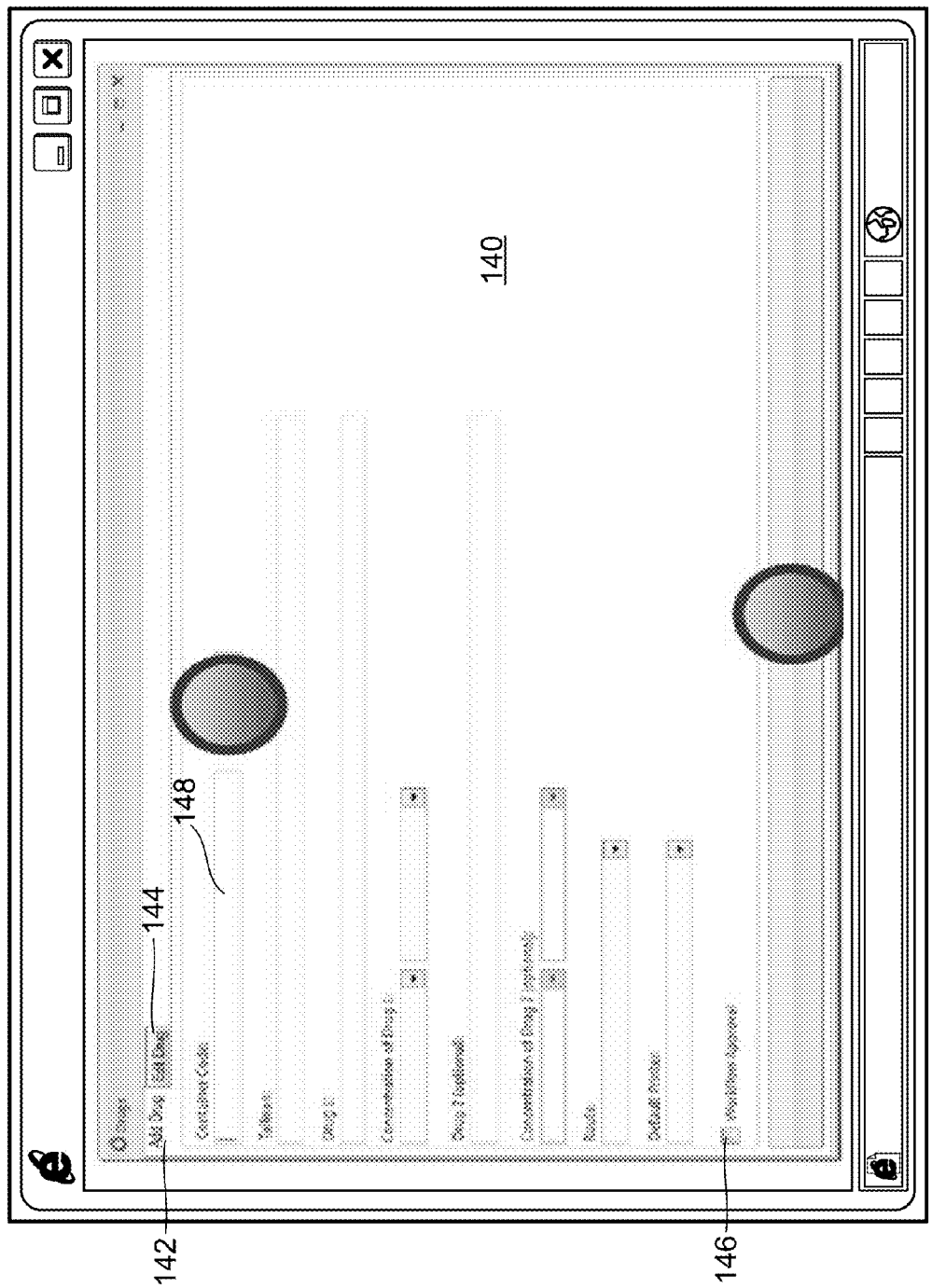
Figure 10:
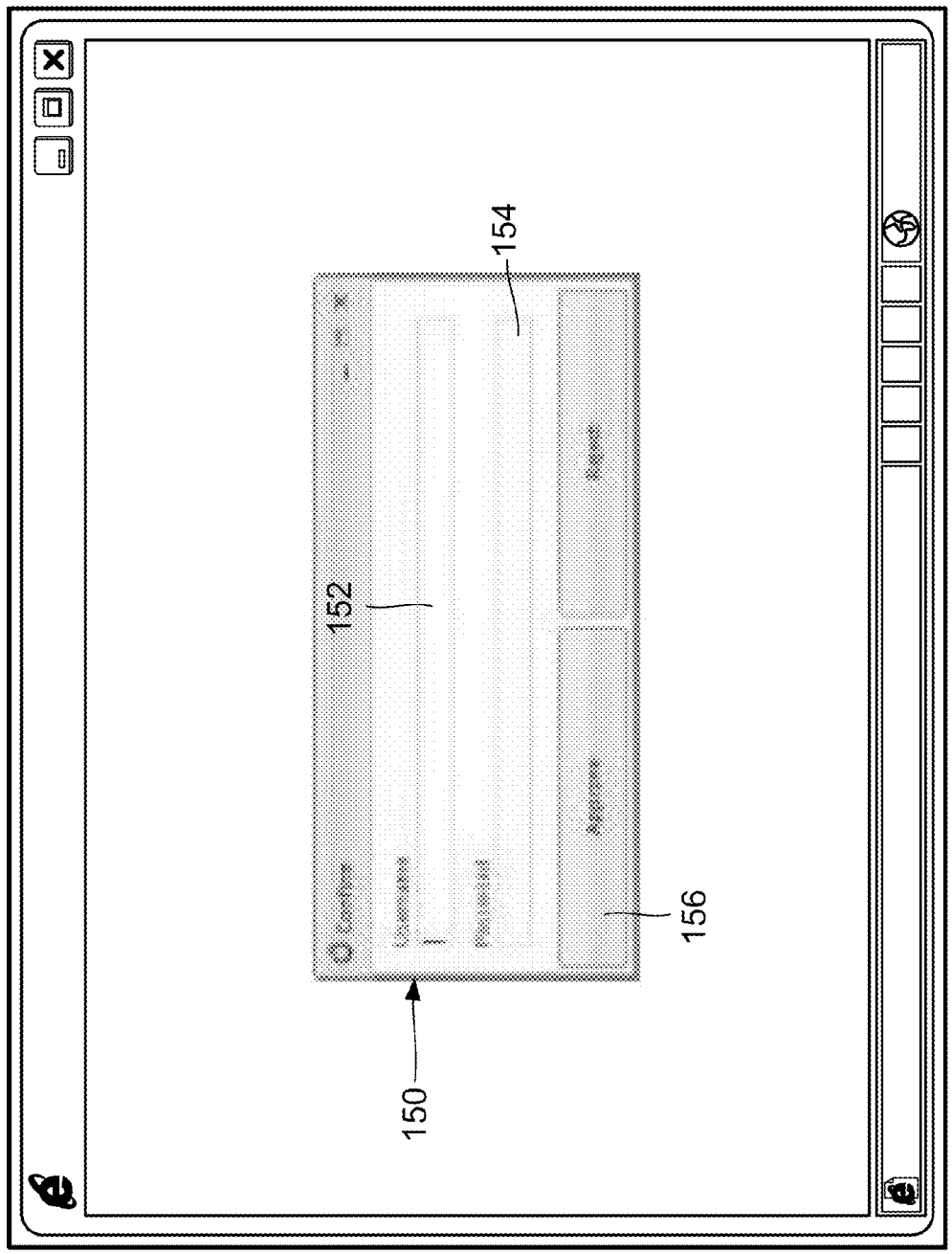
Figure 11:
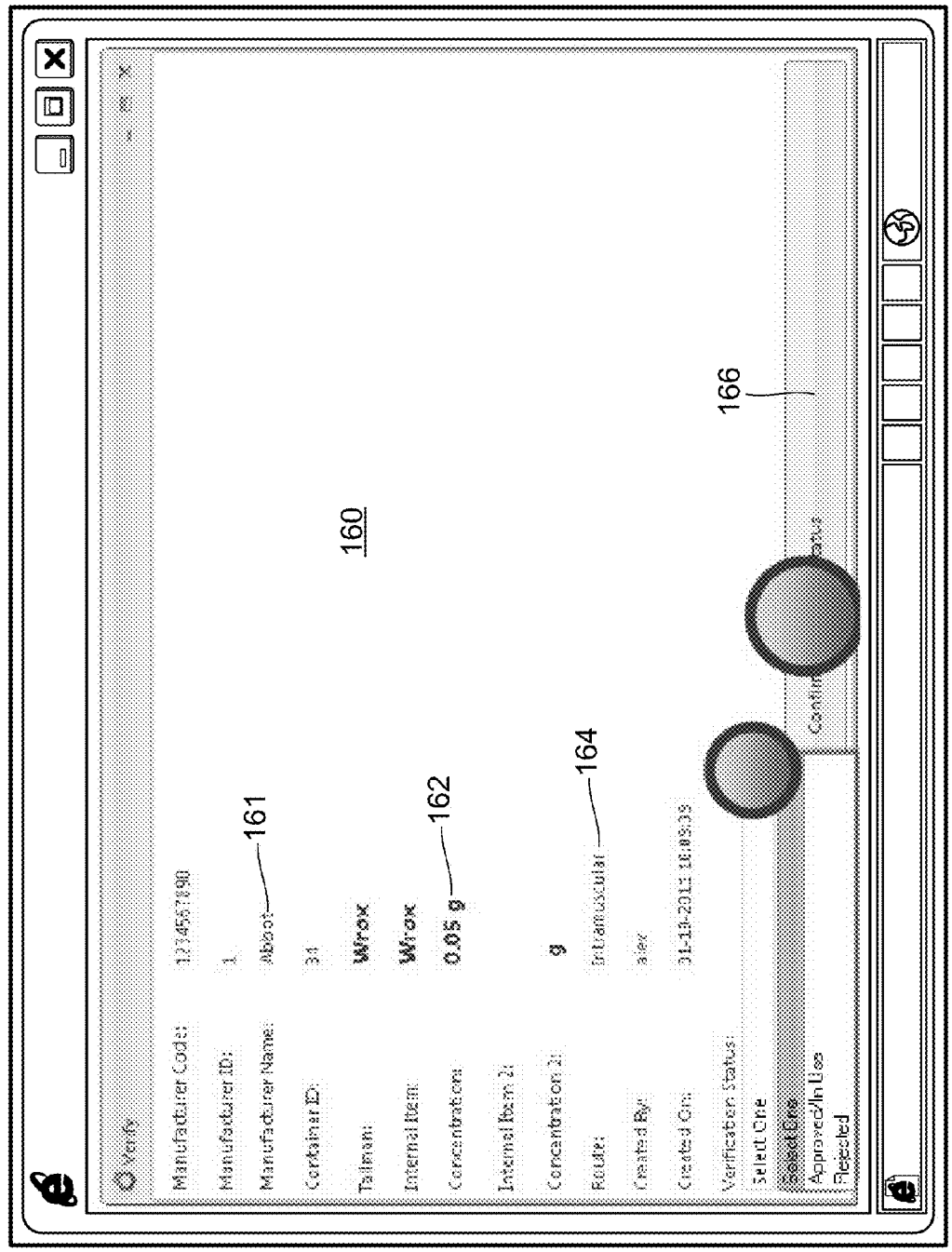

FIG. 6 is a block diagram schematically depicting a method of labeling a plurality of primary packages with a label including a machine-readable code encoding at least a portion of information extracted from a machine-readable code provided to a secondary package and at least a portion of supplemental information; and FIG. 7 shows an illustrative example of a flag label on which a machine-readable code is to be printed;

FIG. 8 shows an illustrative example of a label comprising a plurality of portions, optionally different-shaped portions, on which a machine-readable code can be printed to be applied to a primary package in a manner that does not significantly obscure, or obscure any portion at all, existing label information;

FIG. 9 shows an illustrative example of a drug management interface allowing the addition and editing of drug entries in a database that is to be subsequently referenced to prepare labels for labeling a dose of a drug to be administered to a patient;

FIG. 10 shows an illustrative example of a Workflow Approval interface that can receive Workflow Approval to allow a restricted label requiring Workflow Approval to be made available for use; and FIG. 11 shows an illustrative embodiment of a verification interface.

DETAILED DESCRIPTION OF THE INVENTION

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

Figure 1:
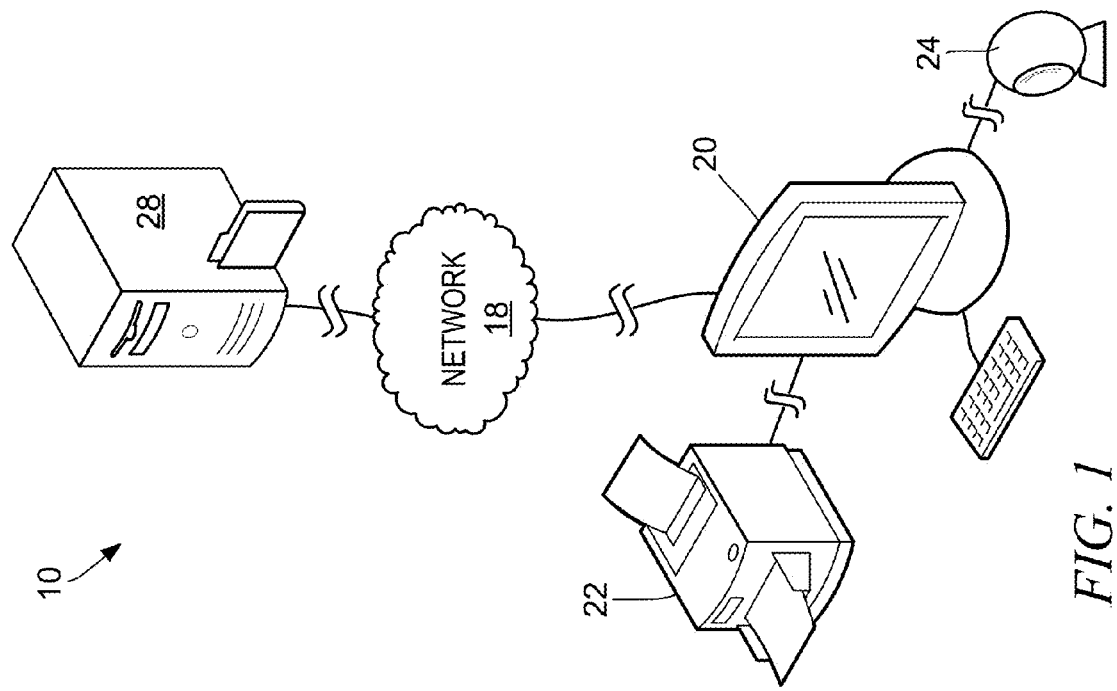
FIG. 1 shows an illustrative embodiment of a networked computer system for extracting information relating to a medicinal substance from a plurality of machine-readable codes, each complying with a different coding standard.

FIG. 1 shows an illustrative embodiment of a networked computer system 10 for extracting information relating to a container storing a medicinal substance 12 (FIG. 4) from a plurality of machine-readable codes 14, 16, each complying with a different coding standard. The computer system 10 appearing in FIG. 1 is a network-connected computer system 10, including distributed devices operatively connected to communicate with each other via network 18 that includes a wide area network ("WAN"), a local area network ("LAN"), or a combination of a WAN and a LAN. For instance, a WAN such as the Internet utilizes widely-distributed public communication channels such as public telephone lines and exchanges to establish communication between networked devices that are distributed over a relatively large geographic area. A LAN, on the other hand, includes locally-networked components located within a relatively confined geographic locality such as a common building, or campus for example. Wireless (e.g., IEEE 802.11 compliant) or dedicated wired (e.g., Ethernet) network channels are typically utilized to establish communication between LAN network devices.

The embodiment of the computer system 10 in FIG. 1 includes a computer terminal 20 operatively connected to a printer 22 and a scanner 24 that is operable to read machine-readable codes. As shown, the printer 22 and the scanner 24 are coupled to the terminal 20 as peripheral devices, but one or both can alternately be integrated as part of the terminal 20. For example, FIG. 3 illustrates an embodiment of a stand-alone computer system 100 for extracting information relating to a medicinal substance from a plurality of different barcodes 14, 16, each representing the information according to a different coding standard. An example of the computer system 100 appearing in FIG. 3 is described in U.S. patent application Ser. No. 12/901,088 to Smka et al., which is incorporated in its entirety herein by reference. The computer system 100 includes a scanner 124 disposed adjacent to an underside of an integrated touch-screen display 125. A printer 122 is also integrally formed as part of the stand-alone computer system 100, which also includes the computational components described below with reference to FIG. 2.

The computer system 100 is described as being a "stand-alone" terminal since it stores the database of medicinal substances locally in the computer terminal 120. The computer system 100 does not necessarily require communication with other terminals and/or devices over the network 18 to extract the information from computer-readable codes that are compliant with a plurality of different coding standards.

The printer 22 can be any printer that can print label content onto label stock. For example, the printer 22 can be a conventional laser, ink jet or dot-matrix printer, a thermal printer, or any other suitable device that can apply label content generated by the computer terminal 20 onto a label that is to be provided to a container 12 that stores a medicinal substance as explained below.

The computer system 100 can be interfaced with plurality of printers 22. Each printer 22 can optionally be configured with a specific label type that is suitable for labeling different shapes and sizes of primary packages 42.

The scanner 24 can be any device that is adapted to interrogate the machine-readable codes 14, 16 and transmit a signal that is to be interpreted by a computer processor for extracting information pertaining to the medicinal substance to be disposed in the container 12. The machine-readable code is described using the barcodes 14, 16 as examples in the illustrative embodiments described below, but is not limited to barcodes. Other illustrative embodiments of the machine-readable codes that can be used with the present technology include, but are not limited to: data stored in RFID tags, an arrangement of alpha-numeric characters, an arrangement of symbols, two-dimensional barcodes, and the like. The scanner 24 can be any device that is compatible with such codes to interrogate the machine readable codes and transmit a signal that can be interpreted to extract the encoded information. However, for the sake of brevity and to clearly describe the present technology, the machine readable codes used in the descriptions herein are the one-dimensional barcodes 14, 16. Accordingly, the scanner 24 will be described herein as a barcode scanner 24.

Each type of machine-readable code may also encode information in compliance with one or more, and optionally a plurality of different standards. The standards with which the different, individual machine-readable codes comply can involve compliance with a particular symbology, a particular format, or a combination thereof. The format and/or symbology selected can optionally also comply with a standard universally adopted in a geographic region of interest for use in labeling medicinal substances. For example, the barcodes 14, 16 can encode information as a Universal Product Code ("UPC") format such as UPC-A, meaning that the numerical string represented by the barcode is formatted as a UPC-A number, which includes 12-digits arranged to uniquely represent the labeled item. The UPC-A formatted number can be physically encoded according to the Data Matrix two-dimensional barcode symbology, which includes a two-dimensional array of black and white cells, or a one-dimensional arrangement of vertical lines separated by spaces, for example. According to the present example, the barcode is said to be standard compliant in that it complies with the UPC-A format, and is represented by the Data Matrix symbology. However, according to alternate embodiments, at least one of the barcodes 14, 16 can be formatted according to a proprietary format having any desired number of characters (e.g., numeric, alphanumeric, alphabetic, etc. . . . ) but represented by a conventional barcode symbology to be considered compliant with a standard. Thus, the present technology can involve interpreting and recognizing a symbology, a format, or both the symbology and the format of the barcode(s) 14, 16, and each barcode 14, 16 may comply with a different standard(s).

As mentioned above, barcodes compliant with the UPC-A standard encode a unique 12-digit number. Other examples include barcodes compliant with an EAN format such as EAN-8 or EAN-13, or any other internationally-recognized and adopted suitable Global Trade Item Number ("GTIN") such as GTIN-8, GTIN-12, GTIN-13 and GTIN-14 established by a standards governing body such as GS1, for example. Other coding standards can optionally be mandated by a governmental entity such as the U.S. Food and Drug Administration ("FDA") in the United States, as well as similar entities in jurisdictions around the world, for example, for labeling medicinal substances to be used in providing medical treatment to patients. An example of one such mandated standard is the National Drug Code ("NDC") number format used to identify medicinal substances intended for human use in the United States. A barcode encoding the NDC number represents a unique 11-digit, 3-segment numeric identifier assigned to each medication listed under §510 of the US Federal Food, Drug, and Cosmetic Act. The segments identify the party that labeling party of the vendor of the medicinal substance, the medicinal substance itself, and trade package containing the medicinal substance. But as explained above, the NDC number can be physically expressed as a two-dimensional Data Matrix, or other desired barcode symbology.

The first portion of the NDC number comprises 4 or 5 digits, and is assigned by the FDA to a party submitting a request for a labeler code. The labeler code is assigned to any entity that manufactures, repacks or distributes a drug product. The second portion of the NDC number is 3 or 4 digits in length, and identifies a specific strength, dosage form, and formulation of the medicinal substance from the entity identified by the first portion of the NDC number. The third portion of the NDC number is 1 or 2 digits in length, and identifies the type of package (e.g., primary or secondary package), and the amount of the medicinal substance labeled.

The above coding standards are commonly used in the United States for labeling medicinal substances. Other countries around the world, however, may adopt different coding standards for labeling medicinal substances. For example, another country may encode information pertaining to medicinal substances according to a different coding standard established by the GS1 than the coding standard adopted for use in the United States.

One or more, or a plurality of, or each of the coding standards with which the barcodes 14, 16 comply can optionally include a prefix that is specific to a geographic location, such as the country where the machine-readable code for the medicinal substance labeled originated.

The computer terminal 20 can optionally include a local, non-transitory computer-readable memory 34 (FIG. 2) such as a hard drive storing a database 36 of medicinal substances labeled with the barcodes 14, 16. Being locally disposed relative to a processor 32 (i.e., optionally integrated as part of the terminal 20 itself, but not separated from the processor 32 by a portion of the communication network requiring transmission of such communications between the processor 32 and the memory 34 via a portion of the network), the memory 34 allows the processor 32 to access the memory 34 even during disruptions of network communications. The database 36 can serve as a lookup table relating each medicinal substance therein to information extracted from the barcodes 14, 16. Thus, extracting the information from the barcodes 14, 16, regardless of the coding standards with which they comply, allows the computer terminal 20 to identify the particular medicinal substance labeled. According to an alternate embodiment, the database 36 of medicinal substances can optionally be stored in a remotely-located, network-connected server 28 or other suitable storage device. Storing the database 36 in a network-connected device allows the database 36 to be updated for all connected computer terminals 20 at the server 28 rather than multiple times at each computer terminal 20 included in a network comprising more than one computer terminal 20. Thus, the processor 32 for such embodiments must access the database 36 from the server 28 by communicating over the communication network.

Figure 2:
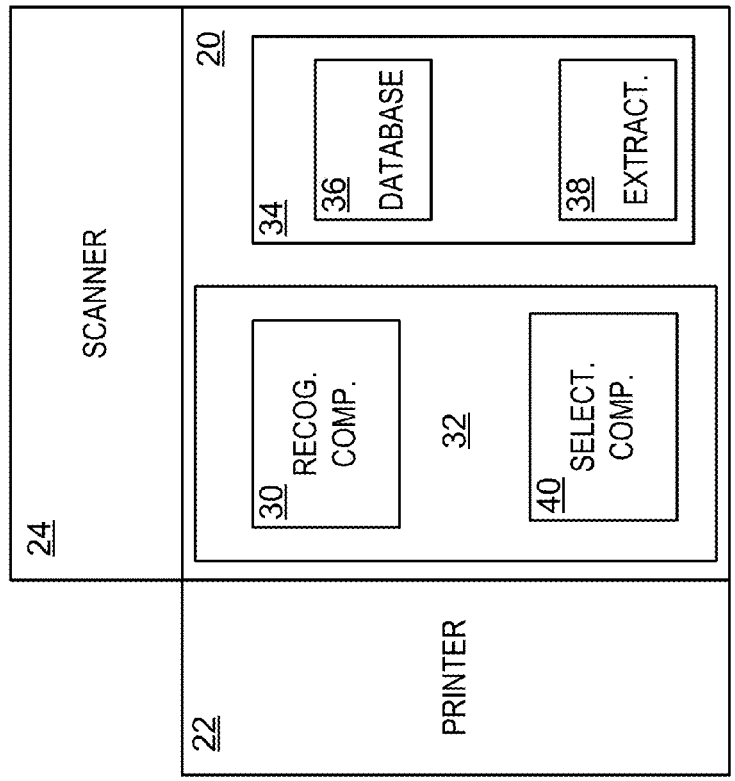
FIG. 2 is a block diagram of an embodiment of a computer system for extracting information relating to a medicinal substance from a plurality of machine-readable codes, each complying with a different coding standard.
Figure 3:
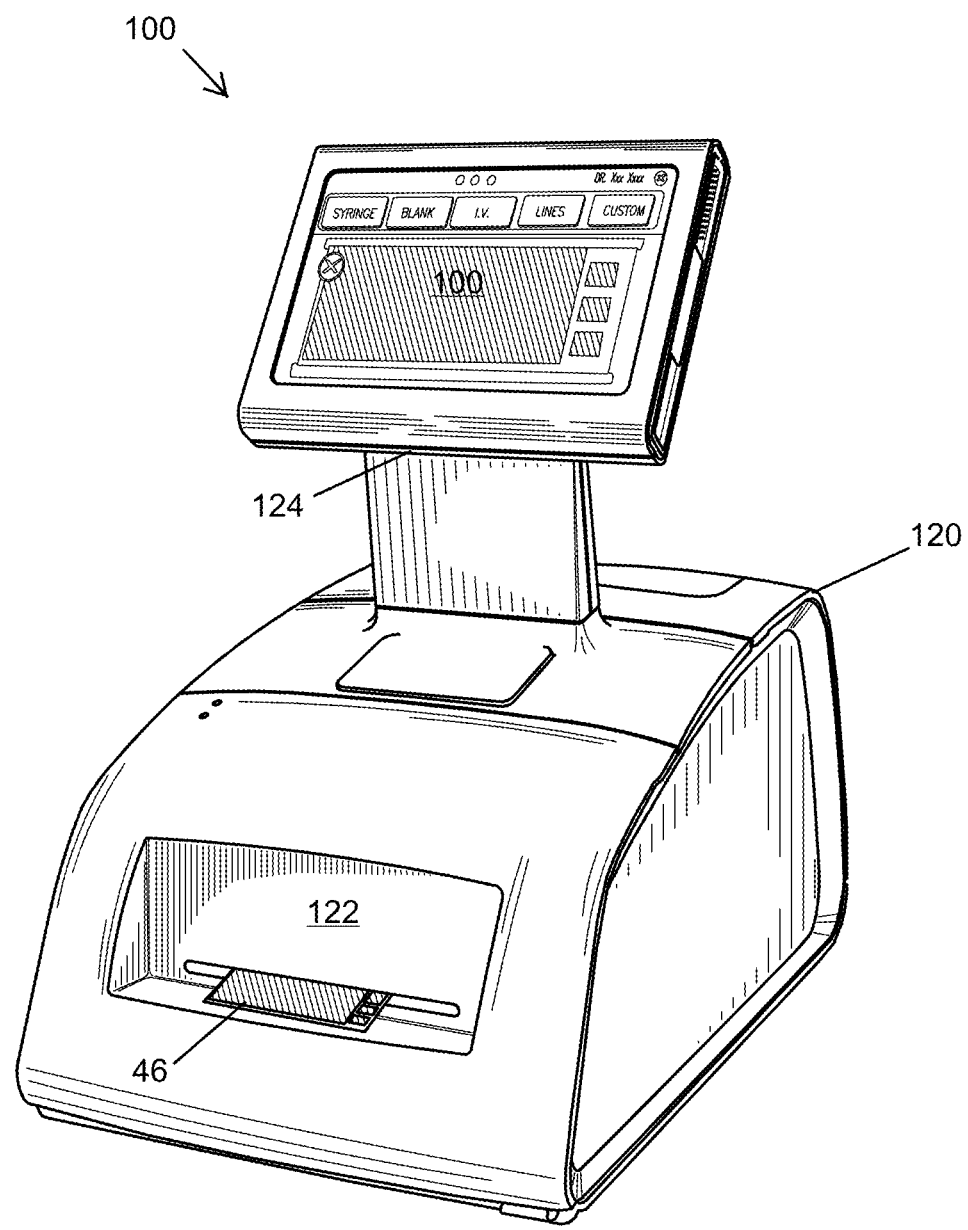
FIG. 3 is a perspective view of a stand-alone embodiment of a computer system for extracting information relating to a medicinal substance from a plurality of machine-readable codes, each complying with a different coding standard.

Shown schematically in the block diagram of FIG. 2, the computer system 10 includes the scanner 24 that is operable to read each of the barcodes 14, 16, which, in the present embodiment, each comply with a different coding standard. In other words, the scanner 24 is capable of reading each of the different barcodes 14, 16, even though an end user may not have an occasion to actually read each and every one of the barcodes 14, 16. By allowing operation of the scanner 24 to be adaptable to read each of the different barcodes 14, 16, the level of customization required of the scanner 24 and associated technology to render the system 10 useful to users in various geographic locations can be minimized. The different coding standards are optionally standards adopted for labeling medicinal substances intended for administration to humans in different countries, however, the information encoded in each of the barcodes 14, 16 includes identifying information that identifies the same medicinal substance. In response to each time the barcodes 14, 16 are interrogated, the scanner 24 transmits a signal that is indicative of the barcode 14, 16 that was scanned.

A recognition component 30, which can optionally be embodied as a computer processor 32 executing computer-executable instructions, makes a determination regarding the coding standard with which each of the barcodes 14, 16 complies to encode the information pertaining to the medicinal substance that is to be extracted. The recognition component can identify a first coding standard of the barcode 14 and a second coding standard of the barcode 16 based on a number of digits represented by each respective barcode 14, 16; based on an arrangement of digits represented by each respective barcode 14, 16; based on an optional prefix represented by each respective barcode 1,4, 16, if present; or any other criteria that allows the recognition component to distinguish between, and identify the coding standard with which the barcodes 14, 16 comply.

In addition to the database 36 of medicinal substances described above, the memory 34 or other suitable storage component can store computer-executable instructions 38 specific to decoding information according to each of the plurality of different coding standards with which the barcodes 14, 16 comply. Although the computer-executable instructions are described as being specific for decoding each of the different coding standards, portions of the computer-executable instructions, such as subroutines, for example, that are executed to perform an operation common to more than one of the coding standards can optionally be utilized or called in the extraction of information according to more than one of the coding standards.

Based on the determination of the particular coding standard with which a scanned barcode 14, 16 complies, a selection component 40 embodied as the processor 32 executing suitable computer-executable instructions, is operable to select the computer-executable instructions specific to the particular coding standard of the scanned barcode 14, 16. Thus, the selection component can select the appropriate computer-executable instructions for extracting the information from each of the plurality of different coding standards. The selected instructions are executable by the computer processor 32 to retrieve the identification of the medicinal substance corresponding to the extracted information from the database 36.

Figure 4:
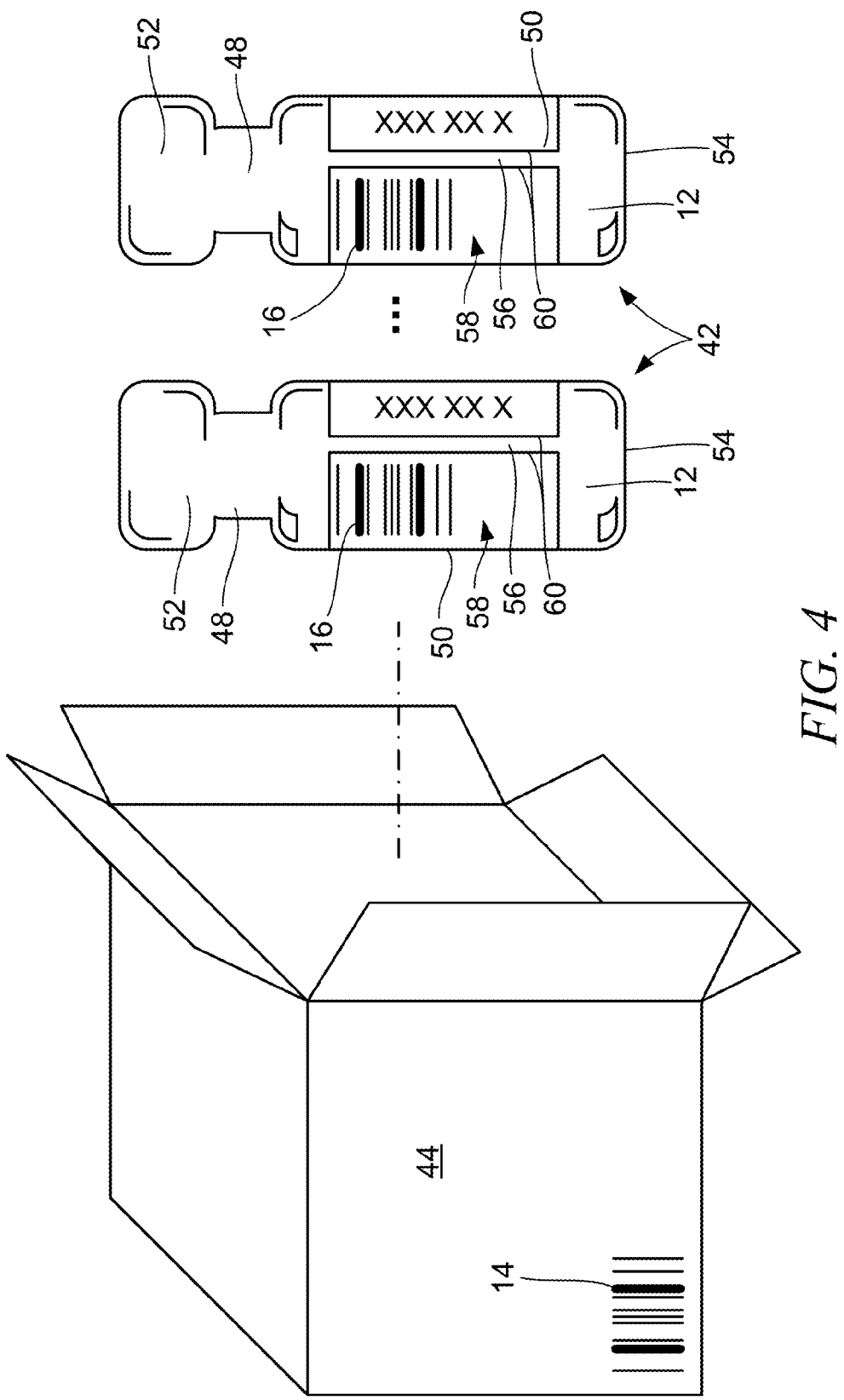
FIG. 4 illustrates a relationship between a primary package containing a medicinal substance and a secondary package in which a plurality of the primary packages of the medicinal substance is delivered.

FIG. 4 illustrates a plurality of primary packages 42 containing a medicinal substance to be labeled, and a secondary package 44 that contains the plurality of primary packages 42. The primary packages 42 represent the "unit dose" or the smallest individual container of the medicinal substance received. The secondary package 44 is the larger quantity of the medicinal substance, containing the plurality of the primary packages 42 that contain the medicinal substance. For example, each primary package may contain approximately 50 mL of the medicinal substance. The primary package may be suitable for only a single usage (i.e., each primary package is intended to be used as a supply of the medicinal substance for a single medical procedure involving a single patient, and then discarded even if all of the medicinal substance has not been removed from the primary package during that medical procedure), or may be suitable for multiple uses (i.e., to serve as the source of the medicinal substance for multiple medical procedures involving different patients). The secondary package 44, on the other hand, may contain from 2 to 12 units, or any other quantity, of the primary package.

The secondary package 44 will typically include the barcode 14, but the primary packages 42 received in the secondary package 44 may not. Accordingly, the method and computer system herein can be utilized to prepare the label 46 to be applied to the primary packages 42 from which doses to be administered to patients can be prepared. Such labels 46 can include the barcode 16, which can be an internal, proprietary code specific to the healthcare facility or other party in possession of the primary packages, or a machine-readable code recognized by different entities. Thus, the individual primary packages 42 can be documented as part of an internal labeling system.

Management of the content included in the database 36 can be performed by an authorized party using the computer terminal 20. There can be a plurality of, and optionally at least four different levels of authorization: administrator, manager, technician, and operator. An administrator is granted full privileges to access, manipulate and otherwise use the data included in the database 36, including the requisite access to set up and configure the computer system 10. A user granted the privileges of an administrator can establish limits on, or grant rights of others to access, manipulate and otherwise use the database data. Administrators can also be authorized to conduct a query of the database 36 using barcode information obtained by scanning the barcode 14 applied to a secondary package 44 by a manufacturer, packager or other source of the medicinal substance packaged therein with the scanner 24, manually entering the barcode information or otherwise initiating a search based on the barcode 14 information. Other administrator rights can include initiating other searches of the database 36 using the computer terminal 20 using search criteria other than the barcode 14, requiring or granting Workflow Approval as described below, performing Verification Workflow as described below, and printing label content to produce labels 46.

A manager can share the privileges afforded to the administrator, except configuring the computer system 10. Generally, a user granted the authorization level of a manager can conduct a query of the database 36 using barcode information obtained by scanning the barcode 14 applied to a secondary package 44 by a manufacturer, packager or other source of the medicinal substance packaged therein with the scanner 24, manually entering the barcode information or otherwise initiating a search based on the barcode 14 information. Other manager rights can include initiating other searches of the database 36 using the computer terminal 20 with search criteria other than the barcode 14, requiring or granting Workflow Approval, performing Verification Workflow, and printing label content to produce labels 46.

Users granted the authorization level of a technician can be authorized to perform all of the actions allowed of a manager, except requiring or granting Workflow Approval.

And users granted the authorization level of an operator can be authorized to perform all of the actions allowed of a technician, except the ability to initiate other searches of the database 36 using the computer terminal 20 with search criteria other than the barcode 14. In other words, the operator's abilities using the computer terminal 20 can be limited to scanning a barcode 14 provided to the secondary package 44 for printing a new label corresponding to the barcode 14, and printing label content to produce labels 46.

Management of the information in the database 36 can include adding drug entries for new drugs, and/or editing existing drug entries. Drugs and drug entries can be added to the database 36 in any desired manner. According to one embodiment, a user with a level of authorization of an administrator or manager can scan a barcode 14 provided to the secondary package 44 using the scanner 24. A signal indicative of the encoded information is transmitted in response, and interpreted by the processor 32. If a drug entry matching the encoded information is not found in the database 36, then a drug entry window including a user interface 140 such as that appearing in FIG. 9 can be displayed by the computer terminal 20. If a matching entry is found, the information from the matching entry can be displayed populating the fields appearing in the user interface 140. In either instance, scanning the barcode 14 provided on the secondary package by the manufacturer, packager or other source of the drugs therein allows the computer terminal 20 to identify that source. The source 161, which in the present example is "Abbot", is presented to the user in a verification interface 160 such as that appearing in FIG. 11, along with other drug-related information such as concentration 162 administration route 164. Presenting the information in the verification interface 160 allows an authorized user to confirm that the drug packaged in the container provided with the barcode 14 is from a trusted source and coincides with what was ordered. If the information is correct the authorized user, who optionally gained access to the verification interface 160 by entering login information such as a username/password combination or other credentials, can select a confirmation button 166 to confirm the accuracy of the displayed information.

The illustrative embodiment of a user interface 140 displayed by the computer terminal 20 in FIG. 9 allows an administrator or manager to add a new drug, such as that arriving in the secondary package 44, to the database 36 and edit an existing drug entry in the database 36. An "add" tab 142 for adding a new drug has been selected in the present example, but existing entries can be edited in an analogous manner by selecting the "edit" tab 144. In adding the new drug entry or editing an existing drug entry, the user can manually enter a Container Code in a code field 148. The container code is to be assigned to a container such as the primary package 42 storing the drug to be associated with the drug entry in the database 36 for identification purposes. The container code can be a manually-input or automatically-generated string of numbers, letters, or a combination thereof. Automatically generated container codes can optionally be generated sequentially or in another patter. For example, a first container code can automatically be assigned a value n, and the very next container code automatically generated can be assigned the value n+1, where n can be any integer or value that can be systematically incremented. Other drug specific information that can be included in the drug entry being added (or edited) includes, but is not limited to: drug name for each drug (e.g., a single name for a simple drug or a name for each drug included in a compound drug or dilution) concentration value, concentration units and route (e.g., injection, infusion, topical application, etc. . . . )

The user interface 140 also includes a check box 146 that, when checked, designates the drug entry being added as requiring Workflow Approval in addition to the information specific to the drug. Some drug entries in the database 36 may be for drugs that exceed a threshold cost (e.g., more than $1,000 per dose) to use, or some drug entries in the database 36 may be experimental, or carry a greater risk and/or severity of adverse side effects than others, for example. To help avoid the use of such drugs indiscriminately or at possibly-inopportune moments, those drug entries and/or drugs can be designated in the database 36 by the authorized party as requiring a manager or other suitably-authorized user to input "Workflow Approval" before the computer terminal 20 will print the label content for such drug entries/drugs onto a label 46. According to one embodiment, the computer system 10 can require Workflow Approval to be input anytime during the label production process for labeling a dose of a drug requiring Workflow Approval before the label is made available to be used. Workflow Approval requires entry of authorization from a suitably-authorized user (e.g., administrator or manager) before a label 46 identifying the corresponding drug is allowed to be printed by a user who lacks such authorization. For instance, the computer system described in U.S. patent application Ser. No. 12/901,088 to Srnka et al. is described as preparing labels to be applied to a syringe containing a drug to be administered to a patient. Use of such a computer system, or the computer system 100 described herein to generate such a label to be applied to a delivery container or a container storing a dose to be administered to a patient can optionally be prohibited until the suitably-authorized user inputs the required authorization for such a label.

Authorization in satisfaction of the Workflow Approval condition can require the suitably-authorized party to enter a username/password combination, or other authenticating information into the computer terminal 20 as a prerequisite to printing a label. For instance, in response to scanning the barcode 16 on a unit dose vial containing a drug requiring Workflow Approval with the scanner 24, a confirmation interface 150 such as that shown in FIG. 10 can be presented by the computer terminal 20. The confirmation interface 150 includes a username field 152 and a password field 154 in which the suitably-authorized individual can enter a username and password, respectively, indicating that permission to generate the label has been granted. After entering the username and password, the authorized user can select the "Approve" button 156 to authorize the label for labeling a dose to be administered to a patient to be printed. The computer terminal 20 can record, in a log, information identifying the suitably-authorized individual who granted authorization for such a label to be printed. The log can be maintained on a locally-accessible computer-readable medium, a network-accessible computer-readable medium remotely-located over the network 18, or a combination thereof for auditing purposes to document the distribution of the drugs requiring Workflow Approval.

According to alternate embodiments, the suitably-authorized individual can input authorization to the computer terminal 20 to generate the label requiring Workflow Approval in any manner other than by entering a username/password combination. For example, the suitably-authorized individual can read a barcode or other such computer-readable code provided on an identification badge using the scanner 24 of the computer terminal 20 being used to generate the label. For other embodiments, a biometric reader such as a fingerprint reader can capture an image of a fingerprint of the suitably-authorized user as authorization.

Any changes to the database 36 (e.g., added or edited drug entries) can be exported as an export file to be stored by a predetermined non-transitory, computer-readable medium. The export file can include only the additions, edits or other changes as an update to data included in a prior export file, or can include all content included in the database 36 including any additions, edits or other changes, which can optionally be highlighted. To make the export file usable by other applications, the data included therein can be arranged in a predetermined format compatible with such other applications. For example, the export file can be a comma-delineated file (e.g., comma-separated-values ("CSV") file) where data is arranged in lines that represent individual rows or records, and in different columns that are separated by a comma. Exportation of the data, regardless of the content or format, can occur automatically when the user with authorization to add/edit drug entries logs out or otherwise terminates an active session using the computer terminal 20. According to alternate embodiments, the data can be manually exported by the user.

Similarly, data can be imported in a CSV file, or other import file having a predetermined format that the computer terminal 20 is configured to recognize, and optionally stored directly to the database 36.

Figure 5:
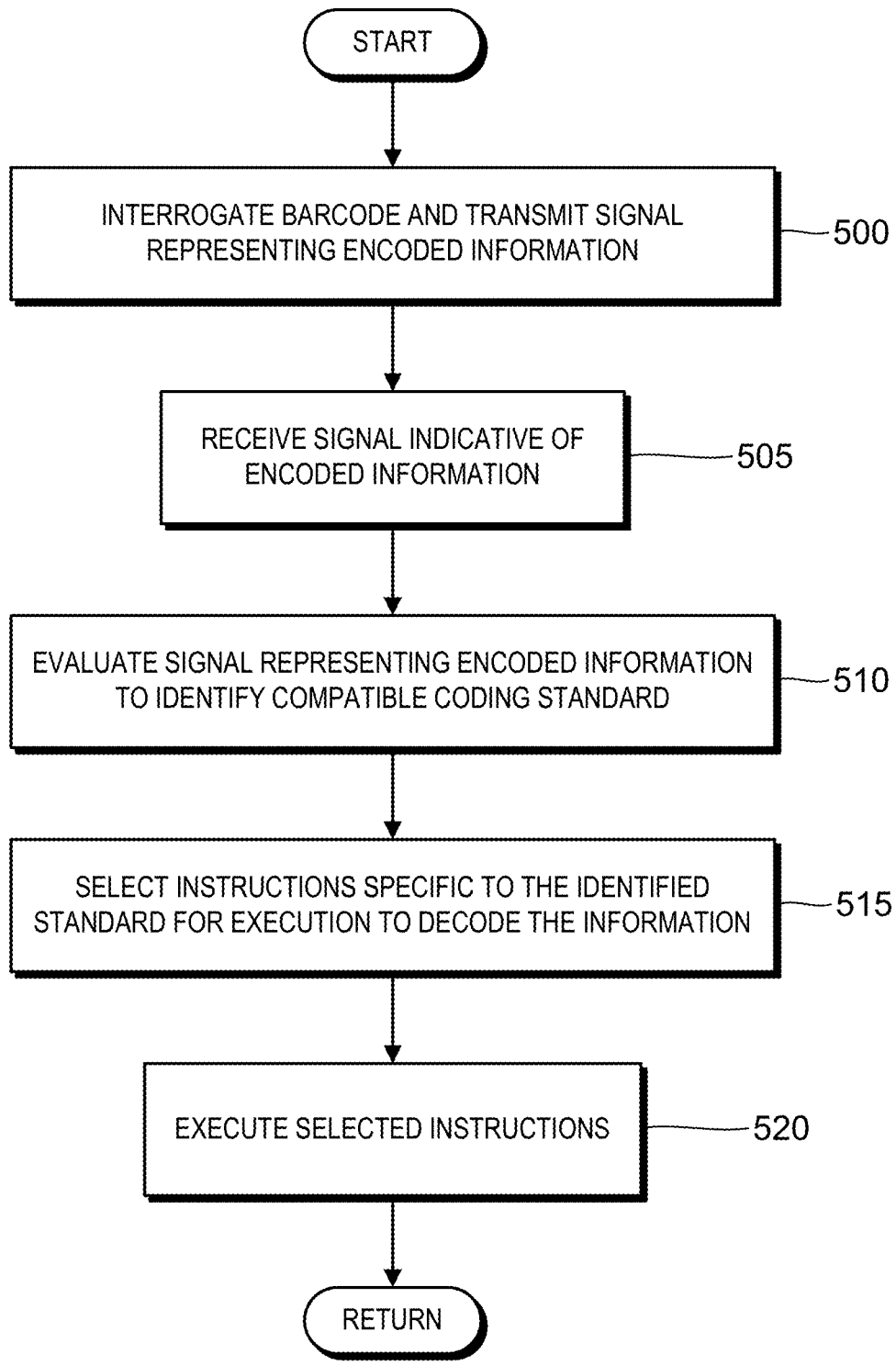
FIG. 5 is a block diagram schematically depicting a method of extracting information about a medicinal substance encoded according to a plurality of different coding standards.

FIG. 5 includes a flow diagram schematically illustrating the method of extracting information from the barcode 14, which may encode information according to different coding standards depending on the country of origin (and/or the destination country) of the secondary package 44. To determine the proper extraction technique for reading the barcode 14 and identifying the medicinal substance, the method begins when the scanner 24 interrogates the barcode 14 at step 500. Interrogating the barcode 14 causes the scanner 14 to receive the encoded information to be used to identify the medicinal substance contained within the secondary package 44 from the barcode 14 at step 505. This encoded information is represented by a signal transmitted by the scanner 24 to the computer terminal 20, which receives the signal to identify the medicinal substance. The recognition component 30, or other portion of the computer terminal 20 or computer system 10, evaluates the signal indicative of the encoded information transmitted in response to interrogating the barcode 14 and identifies the coding standard with which the barcode 14 complies at step 510. The coding standard can be identified from among a plurality of different coding standards based on information about each of the plurality of coding standards stored in the memory 30 or other storage device. This information can include differences among the plurality of different coding standards that can be used to distinguish between them, a signature of each of the coding standards, etc. . . .

Once the coding standard of the barcode 14 has been identified, the computer system 10, particularly a selection component 40, selects at step 515, the computer-executable instructions specific to the identified coding standard from the database 36 storing a library of available computer-executable instructions specific to each of the different coding standards. The computer processor 32 or other processing portion of the computer system 10 executes the selected computer-executable instructions specific to the identified coding standard at step 520 to extract the identity of the medicinal substance according to the identified standard.

Although the information decoded from the barcode 14 is described as including the identity of the medicinal substance, the information can include at least one of: a concentration of the medicinal substance, a lot number of the medicinal substance, a number of primary packages 42 contained within the secondary package 44, a total quantity of the medicinal substance received, a supplier of the medicinal substance, and any other information useful for inventorying and/or dispensing medicinal substances utilized in the medical treatment of human patients. As described in detail below, any portion, or optionally all of such information can be utilized by the computer system 10, such as by the computer terminal 20, for example, to print a label 46 (FIGS. 3, 7 and 8) including a machine-readable code representing at least a portion of that information.

According to an alternate embodiment, the secondary package 44, in FIG. 4 is labeled with the barcode 14, which itself may encode information in compliance with the different coding standards on a country-by-country basis, or even in different regions within the same country. The primary package 42 may arrive bearing the barcode 16 encoded according to a coding standard appropriate for the destination and/or origin of the primary package 42 containing the medicinal substance, or may lack a barcode altogether. Thus, it may be desirable to print a label 46 (FIGS. 3, 7 and 8) bearing a machine-readable code such as the barcode 45 to be applied to the primary package 42 for internal inventory-management and/or documentation purposes. The labels are referred to generally at 46, and specifically in FIG. 7 at 46a, and specifically in FIGS. 8 at 46b and 46c. The embodiment of the label 46a in FIG. 7 can optionally be sized and configured for application around a neck portion 48 (FIG. 4) of the primary packages 42, which is has a lateral dimension in the radial direction that is less than that of a medicinal-substance-storage portion 50 of the primary package 42 and is disposed between the medicinal-substance-storage portion 50 and a dispensing portion 52 of the primary package 42. As shown in FIG. 7, the label 46a can be releasably-adhered to a release layer provided to a carrier 47. For instance, the release layer may include a wax-like finish to which an adhesive provided to an underside of the label 46a does not adhere to as strongly as a non-release surface such as paper and/or glass, for example. The carrier 47 can also optionally bear other printed content including at least one of the name 49, concentration 51, a lot number 55, and/or expiration information 57 pertaining to a first drug stored in the primary package 42. If there is a drug combination in the primary package 42, at least one of the name 59 and concentration 61 of a second drug in the primary package 42. This other printed content can optionally appear on the label in human-readable form on carrier 47, such as alphanumeric characters (i.e., is readable with the naked eye, without the assistance of a computer input device such as the scanner 24 or other computer device for reading machine-readable codes).

The label 46a can be separated from a surrounding portion of the carrier 47 via a perforation 65 (represented by broken lines in FIG. 7) that allows for clean removal of the adhesively-backed label 46a from the carrier 47 by hand. The label 46a includes an elongated band portion 67 that can be suitably sized to extend substantially-entirely around the neck portion 48 of the vial 54. A centerline 69 can be printed (or come pre-printed by the label manufacturer) along the band portion 67 adjacent to the midpoint of that band portion 67. Thus, a user can apply the label 46a to the neck portion 48 by positioning the centerline 69 at approximately the middle of the neck portion 48 and extending the band portion in each direction away from the centerline 69 around the neck portion 48. Doing so allows flag-shaped end portions 71 arranged at opposite ends of the band portion 67 and bearing the barcode 45 to be brought together such that the adhesive provided to the underside of one end portion 71 adheres to the adhesive provided to the underside of the other end portion 71. If the centerline 69 is located at the approximate middle of the neck portion 48 and the band portion wrapped in each direction around the neck portion 48, the two end portions 71 will be approximately arranged to mirror each other and form a clean label.

Each end portion 71 can optionally be provided with one or more, and optionally a plurality of the barcodes 45, each representing the same information, such as at least a portion of the printed content appearing on the carrier 47. Embodiments including the plurality of barcodes 45 offer a degree of redundancy to minimize the likelihood that the encoded information is not readable due to damage to, or other corruption of the label 46a. The presence of the printed content on the carrier 47 helps to ensure a proper understanding of the information encoded by the barcodes 45 until a time when the label 46a is removed from the carrier 47 to be applied to the vial 54. For the embodiment in FIG. 7, the band portion 67 can include a transverse dimension X of approximately 0.2 inches or less, or approximately 0.1 inches or less to be received about the neck portion 48 of the vial 54 between the dispensing portion 52 and the medicinal-substance-storage portion 50. The end portions 71 can each optionally have a transverse dimension Y of approximately 0.5 inches or less, approximately 0.4 inches or less, approximately 0.3 inches or less, or approximately 0.2 inches or less, for example.

According to alternate embodiments as shown in FIG. 8, the label 46c supported by the carrier 47 can be substantially round in shape, and sized and configured to be adhesively applied to a bottom surface 54 of the primary packages 42. According to yet other embodiments, the label 46b can be substantially rectangular in shape, and sized and configured to be applied to a seam portion 56 adjacent to, or between opposite ends 60 of an existing label 58 applied to extend at least partially around the medicinal-substance-storage portion 50 (e.g., along a seam of an existing label for example) of the primary packages 42 by, or on behalf of a vendor or supplier of the medicinal substance, or a combination thereof. In each of such embodiments, the label 46b, 46c can be applied to the primary packages 42 in a manner that does not significantly conceal the information appearing on the existing label 58. Just as for the embodiment shown in FIG. 7, the carrier 47 in FIG. 8 can optionally also include the printed content described above (e.g., name 49, 59 and/or concentration 51, 61 of first and second drugs, lot number 55, expiration information 57, any combination thereof, etc. . . . ). The labels 46b, 46c can each optionally be separated from the surrounding portions of the carrier 47 by perforations to facilitate removal of the labels 46b, 46c therefrom. According to alternate embodiments, the labels 46b, 46c can each optionally be die cut, and thereby separated from the surrounding portions of the carrier 47.

A method of generating label content for preparing the label 46 is schematically illustrated in FIG. 6. Similar to the method described with reference to FIG. 5, the present method includes using the scanner 24 to interrogate the barcode 14 on the secondary package 44 at step 600. Again, interrogating the barcode 14 causes the scanner 24 to receive the encoded information to be used to identify the medicinal substance contained within the secondary package 44 from the barcode 14 at step 605. This encoded information is represented by a signal transmitted by the scanner 24 to the computer terminal 20, which receives the signal to identify the medicinal substance. The recognition component 30, or other portion of the computer terminal 20 or computer system 10, evaluates the signal indicative of the encoded information transmitted in response to interrogating the barcode 14 and identifies the coding standard with which the barcode 14 complies at step 610. Once the coding standard of the barcode 14 has been identified, the computer system 10, particularly a selection component 40, selects at step 615, the computer-executable instructions specific to the identified coding standard from the database 36, or other repository storing a library of available computer-executable instructions specific to each of the different coding standards. The computer processor 32 or other processing portion of the computer system 10 executes the selected computer-executable instructions specific to the identified coding standard at step 620 to look up and extract the identity of the medicinal substance from the database 36 according to the identified standard.

Just as with the previous embodiment, other information pertaining to the medicinal substance can be extracted and obtained from the database 36 based on the barcode 14 provided to the secondary package 44 in addition to the identity of the medicinal substance. In the present embodiment, the information from the barcode 14 is supplemented, at step 625, with supplemental information entered into the computer system 10 by a user at a time when the label 46 is being prepared, or stored in the database 36 by an authorized user when the information pertaining to the drug identified by the barcode 14 was entered into the database 36. For example, the user can input at least one of: an expiration date, an inventory date, a concentration of the medicinal substance, an identification of the user generating the label 46 or otherwise involved with handling and/or administering the medicinal substance, a quantity of the medicinal substance contained in the primary package to be labeled with the label 46, and any other information desired by the user and/or health care facility. The computer system 10 supplements or otherwise establishes a relationship between the information from the barcode 14 and the supplemental information in the database 36.

Entry of the supplemental information can be manual, such as by typing the desired information, for example. Or, entry of the supplemental information can be automated, such as automatically including in the supplemental information an identifier such as the user's name, for example, which is entered into the computer system 10 by scanning an ID card bearing a barcode encoding the user's identity, or by recognizing the user's identity from login information entered by the user when gaining access to the computer system 10.

Label content, including at least a portion of at least one, and optionally both of the information extracted from the barcode 14 and the supplemental information to be printed on the label 46 is generated at step 630. The label content includes a barcode or other machine-readable code that can be scanned by scanner 24 or another compatible scanner. Scanning the barcode on the label 46 allows the computer system 10 to extract not only the information from the barcode 14, but also the supplemental information encoded in the barcode on the label 46. The label content generated at step 630 can also include human-readable and understandable content, comprising alpha-numeric characters that can optionally be duplicative of the information encoded in the barcode on the label 46. Further, the label content generated for application onto the label 46 can optionally be complaint with a medicinal substance labeling standard established by a governing body, such as the FDA or a trade organization for example, that establishes mandates for labels applied for labeling medicinal substances to be administered in providing medical treatment to humans.

The label content generated at step 630 is printed by the printer 22 onto the label stock to be applied to the primary packages 42 at step 635. The number of labels 46 printed can optionally be determined based on information from the barcode 14 or the supplemental information. For example, if the barcode 14 indicates that there are 12 primary packages within the secondary package 44 bearing the barcode 14, the computer system 10 can optionally automatically be configured to print 12 labels 46.

Additionally, the barcode 14 applied to the secondary package 44 can optionally encode information compliant with a first coding standard, and the barcode or other machine-readable code included in the label content generated at step 630 can optionally encode information in a manner that: is not compliant with any established coding standard (i.e., is generated pursuant to an ad hoc standard for the entity maintaining an inventory of the medicinal substance), is compliant with a coding standard different from the first coding standard, or is also compliant with the first coding standard.

Although the information decoded from the barcode 14 is described as including the identity of the medicinal substance, the information can include at least one of: a concentration of the medicinal substance, a lot number of the medicinal substance, a number of primary packages 42 contained within the secondary package 44, a total quantity of the medicinal substance received, a supplier of the medicinal substance, and any other information useful for inventorying and/or dispensing medicinal substances utilized in the medical treatment of human patients.

According to each of the embodiments described herein, a display device such as a computer monitor operatively connected to the computer terminal can present the user with information extracted from a machine-readable code for confirmation purposes. For example, a number of the primary packages 42 enclosed within the secondary package 44 extracted from the barcode 14 can be displayed by the display device. A confirmation entry can optionally be required from the user, confirming the accuracy of the displayed information. Any portion, or all of the information extracted via a machine-readable code can optionally be displayed for such confirmation purposes.

Although the embodiments described above transmit information that relates to the primary packages 42 over a computer network, alternate embodiments can optionally involve transporting any portion of, or all of such information using a readable, writeable media such as USB flash drive, CD-R, CD-ROM, shared network drive or other such media that can be used to transfer data from one computer system to another. Computer system 100 can store and utilize the received information for the purpose of printing labels for other containers that will be used to hold the medications originating from the primary packages 42. Examples of such containers include syringes that are filled with the medication from the primary package and labeled with appropriate information for identification by a medical professional before administration to a patient.

As previously described, each primary package 42 can have an existing label 58. The existing label 58 can provide information specific to the contents of the primary package 42 in human-readable form. For example, a primary package containing a medication can have an existing label that contains human-readable information required for a medical professional to identify the name, concentration, quantity and other relevant information about the medication in the package. In such cases where the existing label 58 contains human-readable information but no machine-readable codes, it may be necessary to apply a label 46 printed as described above with machine-readable codes to the primary package 42 for applications that can use the machine-readable codes. For example, computer system 100 can read barcodes on primary packages such as vials of medication and print labels for syringes that are filled with medication from the vial. Given the primary packages 42 and the existing labels 58 can have different shapes and sizes, the shape, size and location of the label 46 on the primary package 42 may be limited. Specifically, the label 46 can optionally be placed on the vial or other primary package 42 so as not to obscure any important or other existing human-readable information on the existing label 58. Minimizing the size of the label 46 is therefore desirable to provide increased flexibility when placing the label 46 on primary packages 42 of differing sizes. One method to reduce the size of the label 46 is to only include the machine-readable code on the secondary label. However, since the labels 46 are typically printed first and then applied to the primary packages 42 at a later time, the lack of any human-readable information associated with the label 46 can result in the wrong label 46 being applied to the wrong primary package 42.

To minimize such confusion, the label 46 containing machine-readable codes can be printed with the accompanying carrier 47 that contains the human-readable information described in detail above to identify the primary package 42 intended to receive the label 46. The label 46 with the machine-readable codes and the carrier with human-readable information are positioned in close proximity to each other such that a definitive visual association between the label 46 and the carrier 47 is possible. The label 46 can be separated from the carrier 47 and applied to the primary package 42.

The variations in the sizes and shapes of primary packages 42 and the existing labels 58 can make applying the label 46 difficult. For example, a round vial containing medication may have an outer diameter of 0.5 inches and a height of 1.0 inches. Applying a label 46 that contains a single printed barcode to a small, cylindrical vial may result in a wrinkle or fold in the label that is in the region of the barcode. This can interfere with the ability of a scanner to read the barcode.

In another embodiment, the label 46 can contain two or more machine-readable codes to provide redundancy such that damage or irregularities to one of the machine-readable codes will not interfere with the operability of the other machine-readable codes. When multiple machine-readable codes are included on the same label 46, they are not required to be duplicates of each other, but must at least contain the same encoded information necessary for identifying the primary package 42. For example, a label 46 can contain two barcodes that encode the same identifying information about the primary package with each barcode using a different barcode symbology (e.g. Data Matrix and Code 39). A wrinkle, fold or damage in the label 46 that is in the region of one barcode will not interfere with the ability of a scanner to read the other barcode.

Regardless of whether the information to be encoded by the machine-readable code 16 to be printed and applied to the vial 54 or other primary package is obtained by reading the barcode 14, by receiving a transmission over a communication network, or any other means, the barcode 16 to be printed and applied to the primary package 42 can optionally be represented by a conventional symbology such as the Data Matrix symbology for example, but can optionally be formatted in a proprietary format. For instance, it may be desirable to avoid a scenario where the printed barcode 16 to be applied to the vial 54 can be interpreted to represent a first medicinal substance when interpreted according to a first format, but erroneously interpreted as a different medicinal substance when interpreted according to a recognized format such as the NDC. The barcode 16 can optionally be printed to include a portion, such as a 1-character site-specific identifier, a 2-6 character site-specific identifier, or other unique identifier that, when interpreted, indicates that the barcode 16 is a proprietary barcode that is to be interpreted as such, and can optionally indicate the particular site (e.g., particular hospital, etc. . . . ) that has adopted the proprietary format of the barcode 16.

According to alternate embodiments, the barcode 16 in the proprietary format can optionally include a number of digits that is different than the number of digits in any internationally-recognized barcode. For example, the NDC format requires each barcode to represent an identification number having 11 digits, and the UPC-A format requires each barcode to represent an identification number having 12 digits. The site-specific format of the barcode 16 can optionally encode a 15-digit identification number that would not be wrongly recognized as a NDC number or UPC-A number.

Yet other embodiments can optionally include a "suffix" that can be included as part of the identifier for a drug represented by a barcode 16, optionally in addition to the site-specific identifier represented by the barcode 16 in the site-specific format. Although referred to as a suffix, the string of characters can optionally be incorporated anywhere into the identifier of a drug, such as at the end of a base string of characters, or at the beginning, in an intermediate portion, distributed throughout the identifier, or otherwise incorporated. For instance, the barcode 16 can include an additional 4 digits that can iteratively represent different "batches" of a given drug. The 4-digit suffix can be incremented any time information about a drug is received. For example, an initial identification number can be assigned to propofol in a concentration of 10 mg/mL. The 4-digit suffix can be designated as "0001" for that drug. Supposing that a barcode 16 is to be printed onto a label to be applied to a vial of propofol having a concentration of 15 mg/mL, a suffix of "0002" can optionally be appended to the same base string of characters representing propofol. A new suffix can optionally be appended to a base portion of an identifier for a drug anytime any information (e.g., concentration, lot number, manufacturer, etc. . . . ) associated with that drug changes. Other embodiments utilize a sufficiently-large suffix, e.g., 6 or more digits in length, that can optionally be incrementally increased to reflect the number of each label 46 being printed for application onto a vial or other package. According to such embodiments, the label 46 printed to be applied to a first vial or package can optionally include the suffix 0000001. Similarly, the label 46 printed to be applied to the next package or vial that contains a different medication can optionally include the suffix 0000002, and so on. The suffix can optionally be incremented for each vial or package of a given drug, or optionally incremented for each label 46 printed, regardless of the drug container on which the label 46 is to be applied. The suffix can optionally be made customizable, and can be assigned any desired value to allow for uniquely labeling drug containers in a manner that is not in accordance with an internationally or nationally recognized standard for labeling with a machine-readable code without departing from the scope of the technology described herein. For example, the suffix, when incorporated into a base portion of an identifier, should not form an identifier with 11 characters that may erroneously be interpreted as a NDC number. Other embodiments can include a barcode 16

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used herein, such term is intended to be inclusive in a manner similar to the term "comprising" as "comprising" is interpreted when employed as a transitional word in a claim.

What is claimed is:

1. A computerized system for identifying a medicinal substance and storing data related to the medicinal substance to be subsequently used in generating a label for the medicinal substance, the computerized system comprising:
- an entry device that is operable to enter data indicative of an identity of the medicinal substance into the computerized system:
- a storage component that stores the data in a database comprising a plurality of entries that each correspond to a different medicinal substance wherein the data stored by the storage component is associated with an entry designated for a restricted medicinal substance that requires workflow approval before a label identifying the restricted medicinal substance can be printed by a labeling device; and
- a processing component that generates label content comprising a computer-readable code encoding information that, when read by a code reader provided to the labeling device, interferes with an ability of the labeling device to generate a delivery container label, and requires the workflow approval to be input to the labeling device before the delivery container label identifying the restricted medicinal substance to be applied to a delivery container is permitted to be generated by the labeling device; and
- an output device that applies the label content comprising the computer-readable code on a primary package label identifying a primary package that stores the restricted medicinal substance from which the restricted medicinal substance is to be removed to prepare a dose in the delivery container to be administered to a patient.

2. The computerized system of claim 1, wherein the entry device comprises a computer-controlled code reader adapted to read a secondary machine-readable code provided to a secondary package for the restricted medicinal substance.

3. The computerized system of claim 2, wherein the secondary machine-readable code is a barcode, and the code reader comprises a barcode scanner.

4. The computerized system of claim 1, wherein the entry device comprises a computer keyboard that allows a user to manually enter the data.

5. The computerized system of claim 1, wherein the storage component comprises a computer memory in local communication with the processing component relative to a communication network to allow local communication between the processing component and the local computer-accessible memory during a disruption of communications via the communication network.

6. The computerized system of claim 1, wherein the storage component comprises a remotely-located, network-accessible computer memory relative to a communication network, wherein communications between the processing component and the remotely-located, network-accessible computer memory are transmitted over the communication network.

7. A method of identifying a medicinal substance and storing data related to the medicinal substance to be subsequently used in generating a label for the medicinal substance, the method comprising:
- receiving data indicative of an identity of the medicinal substance into a computerized system;
- storing the data in a database saved on a computer-accessible storage component provided to the computerized system, the database comprising a plurality of entries that each correspond to a different medicinal substance, wherein the data stored by the storage component is associated with an entry designated for a restricted medicinal substance that requires workflow approval before a label identifying the restricted medicinal substance can be generated by a labeling device;
- generating label content comprising a computer-readable code encoding information that, when read by a compatible code reader provided to the labeling device, interferes with an ability of the labeling device to print a delivery container label, and requires the workflow approval to be entered into the labeling device before the labeling device is rendered operational to generate a delivery container label identifying the restricted medicinal substance to be applied to a delivery container; and
- applying the label content comprising the computer-readable code to a primary package label identifying a primary package that stores the restricted medicinal substance from which the restricted medicinal substance is to be removed to prepare a dose in the delivery container to be administered to a patient.

* * * * *